United States Patent
Salys et al.

(10) Patent No.: US 7,092,766 B1
(45) Date of Patent: Aug. 15, 2006

(54) ACTIVE FIXATION LEAD WITH MULTIPLE DENSITY

(75) Inventors: Scott Salys, Santa Clarita, CA (US);
Peter Fong, Northridge, CA (US);
Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 20 days.

(21) Appl. No.: 10/718,216

(22) Filed: Nov. 19, 2003

(51) Int. Cl.
*A61N 1/00* (2006.01)

(52) U.S. Cl. ...................... 607/127; 607/128
(58) Field of Classification Search ............... 607/127, 607/128
See application file for complete search history.

(56) References Cited

U.S. PATENT DOCUMENTS

| | | | |
|---|---|---|---|
| 4,106,512 A * | 8/1978 | Bisping | 607/127 |
| 4,570,642 A | 2/1986 | Kane et al. | 607/127 |
| 4,649,938 A * | 3/1987 | McArthur | 607/127 |
| 4,667,686 A * | 5/1987 | Peers-Travarton | 607/127 |
| 4,953,564 A | 9/1990 | Berthelsen | |
| 4,972,848 A | 11/1990 | Di Domenico et al. | 607/127 |
| 5,002,067 A | 3/1991 | Berthelsen et al. | 607/120 |
| 5,003,992 A * | 4/1991 | Holleman et al. | 607/120 |
| 5,259,395 A * | 11/1993 | Li | 607/131 |
| 5,342,414 A | 8/1994 | Mehra | 607/127 |
| 5,374,286 A | 12/1994 | Morris | 607/119 |
| 5,456,708 A | 10/1995 | Doan et al. | 607/127 |
| 5,473,812 A | 12/1995 | Morris et al. | 29/825 |
| 5,522,872 A * | 6/1996 | Hoff | 607/119 |
| 5,531,783 A | 7/1996 | Giele et al. | 607/126 |
| 5,575,814 A * | 11/1996 | Giele et al. | 607/127 |
| 5,716,390 A * | 2/1998 | Li | 607/127 |
| 5,942,276 A | 8/1999 | Chivers et al. | 427/2.12 |
| 2003/0028231 A1 | 2/2003 | Partridge et al. | 607/120 |
| 2003/0040787 A1 | 2/2003 | Flynn et al. | 607/122 |

* cited by examiner

*Primary Examiner*—George Manuel
*Assistant Examiner*—Lenwood Faulcon

(57) ABSTRACT

An implantable lead adapted to transmit electrical signals between a connector assembly on a proximal end of the lead and at least one electrode carried by a distal end of the lead comprises a helical fixation element extendable and retractable from the distal end of the lead, the header comprising (a) an inner header part comprising an electrically conductive material that is substantially transparent fluoroscopically, the inner header part having a distal end, (b) an outer header part comprising an electrically insulating material, and (c) a collar attached to the distal end of the inner header part. The collar comprises a material that is substantially opaque fluoroscopically. The collar may be electrically conductive, and electrically and mechanically connected, preferably by means of an overlap joint, to the distal end of the inner header part. The conductive collar thus may be electrically connected to an electrical contact on the connector assembly via the electrically conductive inner header part, whereby the collar may be used for mapping the electrical activity of local body tissue. Alternatively, the collar may be electrically isolated by, for example, covering the outer surface of the collar with an electrically insulating layer.

25 Claims, 3 Drawing Sheets

ACTIVE FIXATION LEAD WITH MULTIPLE DENSITY

FIELD OF THE INVENTION

The present invention relates generally to implantable medical devices for electrically stimulating selected body tissue, and more particularly to improved body implantable electrical leads of the screw-in type for connecting a pulse generator with the tissue to be stimulated.

BACKGROUND OF THE INVENTION

Body implantable electrical leads form the electrical connection between a pulse generator, such as a cardiac pacemaker, and body tissue, such as that of the heart, which is to be electrically stimulated. As is well known, the leads connecting pacemakers with the heart may be used for pacing or for sensing electrical signals produced by the heart, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal tip an electrode designed to contact the endocardium, the tissue lining the inside of the heart. The lead further includes a proximal end carrying an electrical connector assembly adapted to be received by a receptacle in the pacemaker. A flexible cable or coil conductor surrounded by an insulating sheath couples a terminal contact on the electrical connector assembly with the electrode at the distal tip.

To prevent displacement or dislodgment of the tip electrode and to maintain the necessary stable electrical contact between the tip electrode and the endocardial tissue, the electrode must be firmly anchored relative to the tissue. To achieve this, one type of lead, sometimes referred to as an active fixation lead, includes a pointed, extendable/retractable helix adapted to be screwed into the heart tissue to be stimulated. In this fashion, the position of the tip electrode is mechanically stabilized by positively anchoring the lead tip so that it remains securely in place during the lifetime of the implant.

The fixation helix may itself comprise the tip electrode in which case it is electrically coupled by means of a coil conductor to a rotatable terminal contact pin on the connector assembly. Rotational torque applied to the connector pin at the proximal end of the lead is transmitted via the coil conductor to the helix electrode which is thereby screwed into the heart tissue. Removal of the screw-in electrode from the endocardium is effected by counterrotation of the connector pin. Thus, in lead having a screw-in helix electrode, the coil conductor is used not only as a conductor for electrically coupling the connector pin and the helix electrode, but also as a tool for extending or retracting the helix electrode relative to the distal end of the lead during lead fixation or removal by rotating the connector pin. Whether the screw-in helix is electrically active or not, the degree of extension of the helix relative to the lead tip must be easily verified by the implanting physician.

Today's active fixation leads may be generally divided into two categories. Leads in the first category use a non-electrically conductive polymer header to retain the extendable/retractable helix while leads in the second category use a metal header for that purpose. Because of the fluoroscopic transparency of non-conductive polymers, leads of the first kind facilitate the confirmation of the degree of helix extension and retraction. In aid of such visual confirmation, a high-density, radiopaque metal ring is typically attached to the distal end of the polymer header. The ring thus serves as a fluoroscopic helix position marker; it is not electrically active to transfer electrical signals to and from the pacemaker to which the lead is connected.

Leads of the second category have high density metal headers that are not fluoroscopically transparent thus hindering visual confirmation of the degree of helix extension or retraction. Nevertheless, metal headers do have advantages. For example, their electrical conductivity allows cardiac signals generated in the cardiac tissue adjacent to the distal tip of the lead to be sensed for purposes of mapping localized heart activity. In addition, metal headers have greater strength than plastic headers and may be easily machined to form thin but strong header walls thereby making possible leads with small diameter distal ends.

Accordingly, there remains a need for a screw-in type of lead comprising a header that has the electrical and mechanical advantages of metal headers while at the same time allowing for the easy, visual fluoroscopic confirmation of helix extension and retraction afforded by non-conductive polymer headers.

SUMMARY OF THE INVENTION

In accordance with one, specific, exemplary embodiment of the present invention, there is provided an implantable lead adapted to transmit electrical signals between a connector assembly on a proximal end of the lead and at least one electrode carried by a distal end of the lead. The implantable lead comprises a helical fixation element extendable and retractable from a header on the distal end of the lead, the header comprising (a) an inner header part comprising an electrically conductive material that is substantially transparent fluoroscopically, the inner header part having a distal end, (b) an outer header part comprising an electrically insulating material, and (c) a collar attached to the distal end of the inner header part. The collar comprises a material that is substantially opaque fluoroscopically.

Pursuant to other aspects of the invention, the collar may be electrically conductive, and electrically and mechanically connected, preferably by means of an overlap joint, to the distal end of the inner header part. In this way, the conductive collar may be electrically connected to an electrical contact on the connector assembly via the electrically conductive inner header part, whereby the collar may be used for mapping the electrical activity of local body tissue. Preferably, the inner header part may comprise a material selected from the group consisting of titanium, MP35N alloy, stainless steel and an electrically conductive polymer, while the collar may comprise a material selected from the group consisting of platinum, gold, a platinum/iridium alloy and tantalum.

In accordance with another specific, exemplary embodiment, the collar may be electrically isolated, and in this regard, the outer surface of the collar may be covered by an electrically insulating layer.

BRIEF DESCRIPTION OF THE DRAWINGS

The foregoing and other aspects, features and advantages of the invention will be evident to those skilled in the art from the detailed description below, taken together with the accompanying drawings, in which.

DETAILED DESCRIPTION OF THE INVENTION

The following description is of a best mode presently contemplated for practicing the invention. This description is not to be taken in a limiting sense but is made merely for the purpose of describing the general principles of the invention whose scope may be ascertained by referring to the appended claims.

Figure 1:
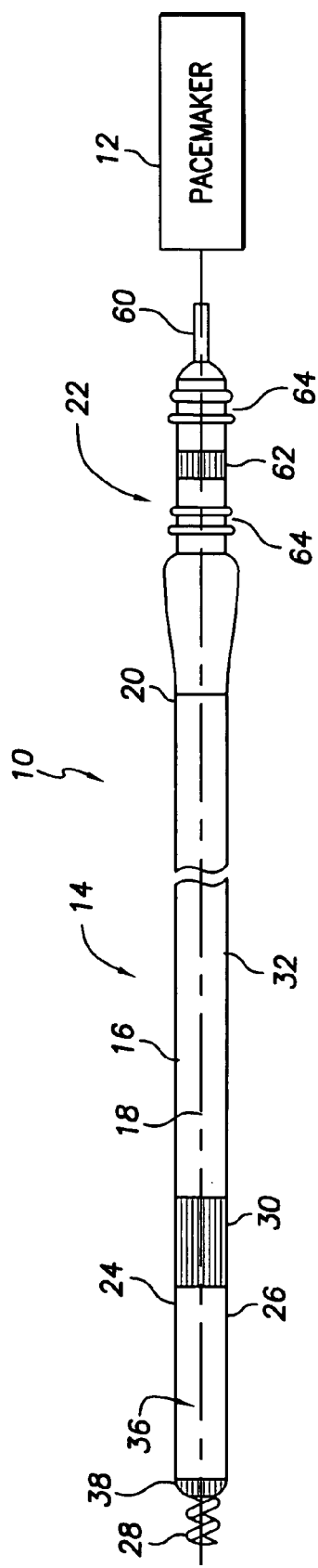
FIG. 1 is a side view of an implantable medical device comprising, generally, a pulse generator and a bipolar, active fixation pacing and sensing lead in accordance with one specific, exemplary embodiment of the present invention.

With reference to FIG. 1, there is shown a specific, exemplary embodiment of the invention comprising an implantable medical device (IMD) 10 including, generally, a cardiac pacemaker 12 and a transvenous, bipolar, active fixation cardiac pacing and sensing lead 14 for connecting the pacemaker 12 with selected cardiac tissue whose electrical activity is to be stimulated and sensed. The lead 14 includes a lead body 16 extending along a central, longitudinal axis 18. The lead body 16 has a proximal end 20 carrying a connector assembly 22 for electrically connecting the lead body 16 to the pacemaker 12. The lead body 16 further comprises a distal portion 24 comprising a header 26, a helical, screw-in fixation element 28 adapted to be extended so as to project from the distal end of the header, and a ring electrode 30 located proximally of the header 26. The helical screw-in fixation element 28 is preferably active electrically so as to function as an electrode when implanted to stimulate selected cardiac tissue such as the tissue of the right ventricle of the heart and/or to sense the electrical activity of the tissue. Consistent with teachings well known in the art, one or more portions of such an electrode may be electrically insulated along its length. Whether electrically active or inactive, when extended or advanced into the selected body tissue the helical element 28 serves to stabilize or anchor the distal portion 24 of the lead body relative to the tissue. For convenience, the helical element 28 will also be referred to in this description as a helix electrode, the preferred form of the element 28.

The lead body 16 is covered by a tubular sheath 32 made of a biocompatible, biostable electrically insulating material such as silicone rubber or polyurethane. The sheath 32 extends between the distal end of the connector assembly 22 and the proximal extremity of the ring electrode 30.

Figure 2:
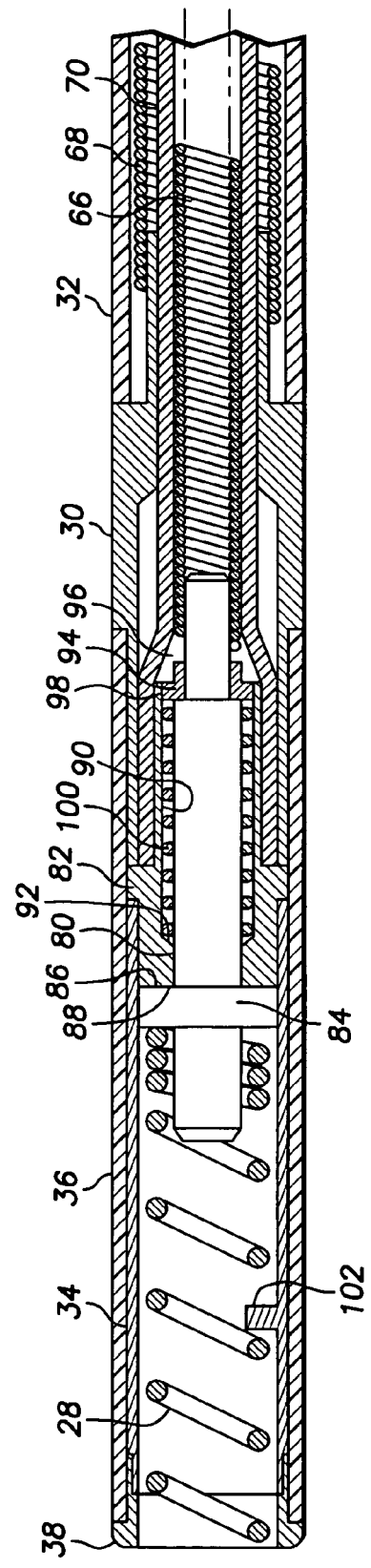
FIG. 2 is an axial cross section view of the distal portion of the lead shown in FIG. 1 with the helix electrode in its fully retracted position.
Figure 3:
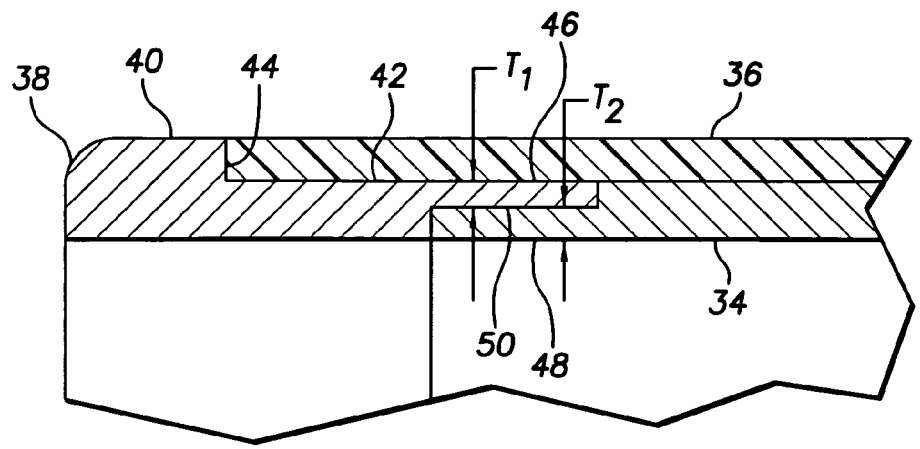
FIG. 3 is an enlargement of a portion of the axial cross section view of FIG. 2.
Figure 4:
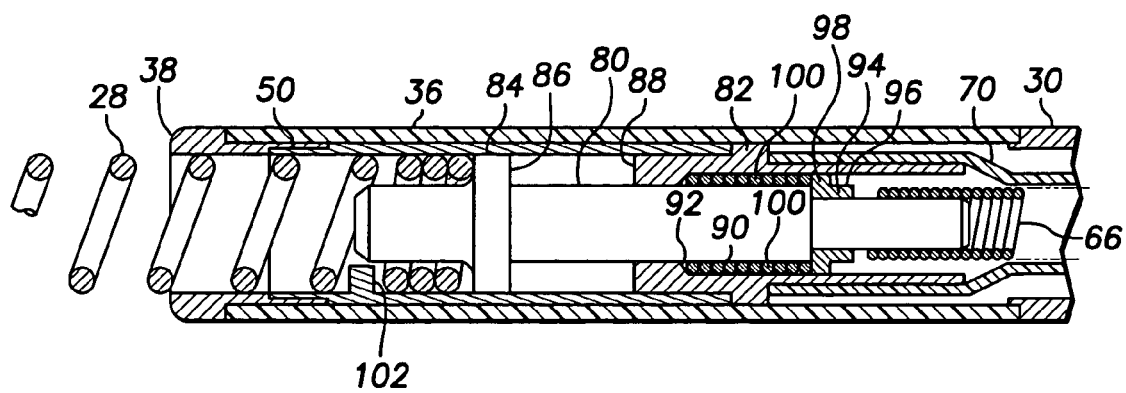
FIG. 4 is an axial cross section view of the distal portion of the lead of FIG. 1 showing the helix electrode in its fully extended position.

With reference now also to FIGS. 2–4, the header 26 comprises an inner, electrically conductive header part 34, an outer, insulating header part 36 of silicone rubber or the like, and a collar 38 attached to the inner header part 34 at the distal extremity thereof. The inner and outer header parts 34 and 36 are preferably in the form of coaxial tubes, as shown in the drawings.

The inner, electrically conductive tube 34 preferably comprises a low density, biocompatible, biostable metallic material such as titanium or a metal alloy such as MP35N alloy or stainless steel that is substantially transparent fluoroscopically. In contrast, the helix electrode 28 and the collar 38 each preferably comprises a high density, biocompatible, biostable, substantially radiopaque metallic material such as platinum, gold or tantalum or an alloy such as platinum/iridium 90/10 or 80/20.

The outer surface of the collar 38 preferably has a permeable or porous texture to increase its effective surface area and to promote rapid tissue ingrowth following implantation. The desired porosity may be provided in various known ways, for example, by sintering platinum particles to the outer surface of the collar 38 or by depositing thereon a coating of titanium nitride (TiN).

The collar 38 may be attached to the distal end of the inner header tube 34 in various ways: FIGS. 2 and 3 show one specific, exemplary attachment. Thus, the collar 38 may comprise a generally tubular structure having an outer cylindrical surface 40 and a proximally-projecting portion 42 having an outer diameter smaller than that of the outer cylindrical surface 40 to define a radially extending, proximal face 44. A proximal end 46 of the collar portion 42 and a distal end 48 of the inner header tube 34 are configured to define an overlap 50 as best seen in the enlargement of FIG. 3. The overlapping ends 46 and 48, which may be formed using conventional machining operations, have thicknesses t1 and t2, respectively. The collar 38 and the inner tube 34 may be joined in various ways; laser welding is preferred. During fabrication, a laser beam, incident upon the high density collar 38 along the outer surface of the overlap 50, is moved circumferentially around the joint to fuse the collar 38 and the inner header tube 34 at the interface of the overlap 50. Filler metal need not be used. Thus, in the example shown, the collar 38 and the inner tube 34 are joined electrically and mechanically.

By using a metal header tube 34 instead of one made of a polymer, the thickness of the overlap 50 may be minimized while preserving adequate strength. For example, the overlap 50 may have a total thickness of 0.004 inch, with the overlapping portions 46 and 48 of the collar 38 and inner tube 34 having equal thicknesses t1 and t2 each contributing 0.002 inch. It will be evident that the thicknesses t1 and t2 need not be the same.

As best seen in FIG. 2, the outer insulating tube 36, installed following the welding step, extends between the proximal face 44 of the collar 38 and the distal extremity of the ring electrode 30. The outer cylindrical surfaces of the collar 38, the outer insulating tube 36 and the ring electrode 30 are preferably substantially flush.

Referring again also to FIG. 1, the connector assembly 22 carried by the proximal end 20 of the lead body 16 is adapted to electrically and mechanically couple the lead body to the pacemaker 12. For the embodiment under consideration, the connector assembly 22 includes terminal contacts in the form of a tubular, rotatable pin terminal contact 60 and a ring terminal contact 62 positioned to engage corresponding electrical terminals within a receptacle in the pacemaker 12. To prevent ingress of body fluids into the receptacle, the connector assembly may be provided with spaced-apart sets of seals 64. Further, in accordance with well known implantation techniques, a stylet or guide wire for delivering and steering the distal portion 24 of the lead body during placement thereof within a chamber of the heart is inserted through the tubular connector pin contact 60 and into a longitudinal passageway within the lead body housing, which passageway may comprise the lumen of a coil dedicated for that purpose or also serving as an electrical conductor connecting the contact pin with the helix electrode 28. Thus, the insulating, tubular sheath 32 encloses a pair of coaxial electrical coil conductors 66 and 68 (FIG. 2) of MP35N or MP35N/Ag alloy or the like, monofilar or multifilar, connecting, respectively, the helix electrode 28 with the rotatable pin terminal contact 60 and the ring electrode 30 with the ring terminal contact 62 on the connector assembly 22. A longitudinally extending insulating tube 70 of silicone rubber, polyurethane, or the like, is disposed between the coaxial coil conductors 66 and 68 to prevent electrical contact between these conductors and between the ring electrode 30 and the inner conductor coil 66.

With reference specifically to FIGS. 2 and 4, the helix electrode 28 is mechanically and electrically connected to the inner coil conductor 66 by means of a helix shaft 80 preferably fabricated of a high density, electrically conductive material such as platinum, gold, tantalum or an alloy such as platinum/iridium 90/10 or 80/20. The proximal end of the helix electrode 28 and the distal end of the inner coil conductor 66 are attached by laser welding or the like, to the opposite ends of the helix shaft 80. The helix shaft 80 is journaled for rotation and axial movement within a sleeve 82 and includes a radially extending flange 84 defining a proximal, radially-extending surface 86 engageable against a distal extremity 88 of the sleeve 82 to limit the retraction of the helix electrode 28. The sleeve 82 is electrically conductive and, like the inner conductive tube 34 to which it is secured, is preferably made of a low density metal or metal alloy of the kinds already described.

The proximal portion of the sleeve 82 has a counterbore 90 terminating at a distal end wall 92. An electrically conductive tubular abutment 94 of MP35N alloy or the like, L-shaped in cross section, has an axial portion 96 welded to the proximal end of the helix shaft 80 and a flange 98 projecting radially within the counterbore 90 of the sleeve 82. Thus, the abutment 94, being secured to the helix shaft 80, is movable rotationally and axially with the helix shaft 80 relative to the sleeve 82.

Contained within the counterbore 90 between the distal end wall 92 thereof and the flange 98 of the abutment 94 is an electrically conductive, expandable/contractable contact member preferably in the form of a metallic compression spring 100 of MP35N alloy or like material. It will be appreciated that electrical continuity is thereby established between the collar 38 and the terminal contact pin 60 on the connector assembly 22, via the inner tube 34, the sleeve 82, the contact spring 100, the L-shaped abutment 94, and the inner conductor coil 66. It will be further appreciated that such electrical continuity will be maintained by the contact spring 100 that extends (FIG. 2) or is compressed (FIG. 4) in response to the extension or retraction of the helix electrode 28. The collar 38 may thus be used to map the electrical activity of selected cardiac tissue during the implantation procedure. It will also be understood that alternatively, the collar 38 may be electrically connected to a terminal contact on the connector assembly other than the contact pin 60.

Projecting radially inwardly from the inner surface of the inner header tube 34 is a post 102 interposed between adjacent turns of the helix electrode 28. In this fashion, rotation of the helix electrode 28 forces the electrode to advance or retract within the lead body header 26. Given the helical sense of the electrode 28, rotation of the electrode 28 clockwise (as viewed from the proximal end of the lead) will cause advancement of the electrode 28 and its extension relative to the collar 38 to a fully extended position (FIG. 4), while counterclockwise rotation will result in retraction of the helix electrode 28 to its fully retracted position within the header 26 as shown in FIG. 2.

Instead of the lead having the bipolar configuration shown, it will be evident that the lead 14 may be unipolar comprising only the helix electrode 28 at the tip. Alternatively, the lead 14 may be multipolar in which case the distal portion 24 of the lead body may carry multiple ring stimulation and/or sensing electrodes as well as one or more cardioverting and/or defibrillating shocking electrodes.

Any conventional lead construction may be utilized so long as it allows for a rotatable member such as the coil conductor 66 extending within the length of the lead body and having a distal extremity attached to the helix electrode.

The specific low density, biocompatible, biostable metal or metal alloy that is used would be selected for its fluoroscopic transparency. For this purpose, titanium is a preferred metal, having a relatively low density of about 4.5 gms/cc. The specific high density, biocompatible, biostable metal or metal alloy that is used would be selected for its relative fluoroscopic opacity that appears as a "shadow" under fluoroscopy. Platinum, for example, is a preferred high density metal, having a density of about 21.1 gms/cc. The object is to attain a usable degree of contrast under fluoroscopy.

In summary, the invention provides for a clearly visible helix extension marker system. In addition, in a preferred form of the invention the collar may be utilized for mapping electrically active local tissue. Metal construction is preferably used for its manufacturability and smaller size advantages. The metals selected are chosen for their differential densities to allow visible, fluoroscopic verification of helix extension/retraction while at the same time permitting visual confirmation of the relative movements and positions of parts within the header, such as the helix shaft 80 and the portion of the helix electrode 28 enclosed within the header 26. The joining of the different density metals may be accomplished in various ways. Besides laser welding, common techniques including crimping may be employed. In addition to these techniques, metals of different densities may be joined by overlaying or depositing one metal on the other. For example, a low-density fluoroscopically transparent metal such as titanium may have a gold coating or gold ring applied to a given region to impart localized fluoroscopic opacity or "shadow".

As mentioned, the present invention allows the header to conduct electrical signals for mapping purposes. Instead of a low density metal or metal alloy, the inner header tube may be fabricated of a low density electrically conductive polymer. Such conductive polymers, which typically exhibit sufficient fluoroscopic transparency for purposes of the present invention, fall into two general categories: intrinsically conductive and conductor-filled. Intrinsically conductive polymers may include polyacetylene, polypyrrole and polyanaline, among others. Conductor-filled polymers may include silicone rubber with embedded metallic, carbon or graphite particles or powder.

It will be evident that the lead depicted in FIGS. 1–4 may or may not be used for mapping the electrical activity of the local cardiac tissue. Where the lead is not used for mapping, the lead's utility resides in the enhanced ability to monitor helix extension and the improved strength of the header while minimizing its outer diameter.

Figure 5:
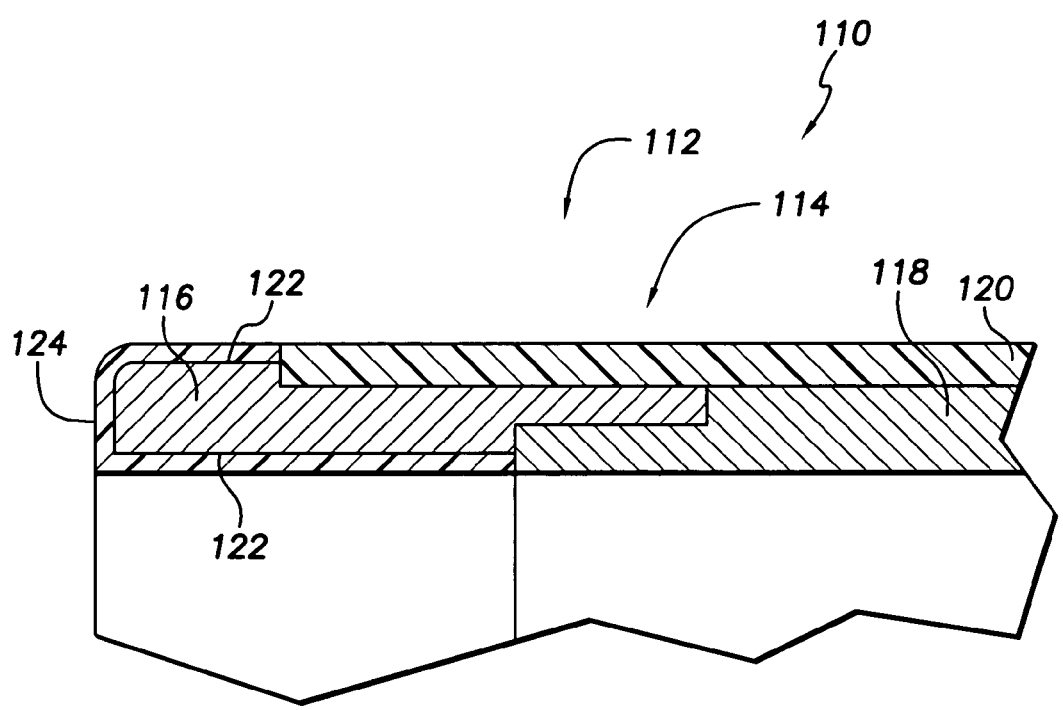
FIG. 5 is an enlarged axial cross section of a portion of a lead in accordance with an alternative embodiment of the invention.

FIG. 5 shows a portion of a lead 110 in accordance with an alternative, non-mapping embodiment of the invention. As before the lead 110 comprises a lead body having a distal end 112 including a header 114 comprising a high density, substantially radiopaque collar 116, a low density, substantially fluoroscopically transparent inner header tube 118, and an insulating outer header tube 120. The header 114 encloses a helical screw-in element, preferably an electrically active, screw-in electrode (not shown). The collar 116, the inner header tube 118 and the outer header tube 120 are preferably made of materials such as those described earlier. The collar 116 has an outer surface 122 that, as seen in FIG. 5, extends around to the interior of the collar and that is covered by an insulating film or layer 124. Accordingly, the insulating layer 124 prevents transmission of electrical signals generated by the local body tissue. The insulating layer 124 may comprise a polymer material such as silicone or parylene that may be applied to the outer surface 122 of the collar 116 in any of a variety of known ways. For example, a silicone composition may be molded to form a sleeve closely fitting the contour of the outer surface 122. Alternatively, parylene may be applied to the surface 122 by vapor deposition. Other insulating materials and techniques for their application will suggest themselves to those skilled in the art. Moreover, expedients other than, or in addition to, the use of an insulating layer on the surface of the collar for electrically isolating the header from, for example, the inner coil conductor 66, will be apparent to skilled artisans.

While several illustrative embodiments of the invention have been disclosed herein, still further variations and alternative embodiments will occur to those skilled in the art. Such variations and alternative embodiments are contemplated, and can be made without departing from the spirit and scope of the invention as defined in the appended claims.

What is claimed is:

1. An implantable lead adapted to transmit electrical signals between a connector assembly on a proximal end of the lead and at least one electrode carried by a distal end of the lead, the lead comprising:
a helical fixation element extendable and retractable from the distal end of the lead, the distal end comprising (a) an inner header tube comprising an electrically conductive material that is substantially transparent fluoroscopically to allow an unobstructive fluoroscopic view of the helical fixation element, the helical fixation element housed within the inner header tube when in a retracted position, and the inner header tube having a distal end, (b) an outer header tube comprising an electrically insulating material, the outer header tube being coaxial to the inner header tube, and (c) a distal tip collar attached to the distal end of the inner header tube, the distal tip collar comprising a material that is substantially opaque fluoroscopically and electrically conductive, and the distal tip collar being electrically coupled to the distal end of the inner header tube.

2. The lead of claim 1 in which:
the inner header tube comprises a material selected from the group consisting of titanium, MP35N alloy, stainless steel and an electrically conductive polymer.

3. The lead of claim 1 in which:
the collar is made of a material selected from the group consisting of platinum, gold, a platinum/iridium alloy and tantalum.

4. The lead of claim 1 in which:
the helical fixation element comprises a helix electrode connected to an electrical terminal contact on the connector assembly.

5. The lead of claim 4 in which:
the helix electrode is substantially opaque fluoroscopically.

6. The lead of claim 1 in which:
the connector assembly comprises a pin terminal contact wherein the inner header tube electrically couples the pin terminal contact to the collar.

7. The lead of claim 1 in which:
the outer header tube has a lumen defined by an inner cylindrical surface, the inner header tube has an outer cylindrical surface, and a diameter of the inner cylindrical surface of the outer header tube is substantially the same as a diameter of the outer cylindrical surface of the inner header tube.

8. The lead of claim 7 in which:
the inner cylindrical surface of the outer header tube directly abuts the outer cylindrical surface of the inner header tube.

9. The lead of claim 1 in which:
the collar is electrically coupled to an electrical contact on the connector assembly via the inner header tube.

10. An implantable lead adapted to transmit electrical signals between a connector assembly on a proximal end of the lead and a distal end of the lead for stimulating selected body tissue, the lead comprising:
a helix electrode extendable and retractable from the distal end of the lead, the helix electrode being electrically connected to an electrical contact on the connector assembly, the distal end comprising (a) coaxial inner and outer tubes, the inner tube having a distal end and being made of an electrically conductive material that is substantially transparent fluoroscopically to allow an unobstructive fluoroscopic view of the helix electrode and the outer tube being made of an electrically insulating material, the helix electrode disposed within the inner and outer tubes when in a retracted position, and (b) a distal tip collar attached to the distal end of the inner tube, the distal tip collar being electrically coupled to the distal end of the inner tube, and the collar being made of an electrically conductive material that is substantially opaque fluoroscopically.

11. The lead of claim 10 in which:
the collar is electrically isolated from the connector assembly.

12. The lead of claim 10 in which:
the inner tube comprises a material selected from the group consisting of titanium, MP3N alloy, stainless steel and an electrically conductive polymer.

13. The lead of claim 10 in which:
the collar is made of a material selected from the group consisting of platinum, gold, a platinum/iridium alloy and tantalum.

14. The lead of claim 10 in which:
the helix electrode is made of an electrically conductive material that is substantially opaque fluoroscopically.

15. The lead of claim 10 in which:
the inner tube electrically couples the collar to the electrical contact on the connector assembly.

16. The lead of claim 10 in which:
the outer tube has a lumen defined by an inner cylindrical surface, the inner tube has an outer cylindrical surface, and a diameter of the inner cylindrical surface of the outer tube is substantially the same as a diameter of the outer cylindrical surface of the inner tube.

17. The lead of claim 16 in which:
the inner cylindrical surface of the outer tube directly abuts the outer cylindrical surface of the inner tube.

18. An implantable lead adapted to transmit electrical signals between a connector assembly on a proximal end of the lead and a distal end of the lead for stimulating selected body tissue, the lead comprising:

a helix electrode extendable and retractable from the distal end of the lead, the helix electrode being electrically connected to an electrical contact on the connector assembly, the distal end comprising (a) coaxial inner and outer tubes, the inner tube having a distal end and being made of a low density, metallic material that is substantially transparent fluoroscopically to allow an unobstructive fluoroscopic view of the helix electrode and the outer tube being made of an electrically insulating material, the helix electrode disposed within the inner and outer tubes when in a retracted position, and (b) a distal tip collar electrically attached to the distal end of the inner tube, the distal tip collar being made of a high density metallic material that is substantially opaque fluoroscopically.

19. The lead of claim 18 in which:

the collar is electrically connected to an electrical contact on the connector assembly via the conductive inner tube, whereby the collar may be used for mapping the electrical activity of local body tissue.

20. The lead of claim 18 in which:

the collar is electrically isolated from the connector assembly.

21. The lead of claim 18 in which:

the inner tube comprises a material selected from the group consisting of titanium, MP35N alloy, and stainless steel.

22. The lead of claim 18 in which:

the collar comprises a material selected from the group consisting of platinum, gold, a platinum/iridium alloy and tantalum.

23. The lead of claim 18 in which:

the helix electrode is substantially opaque fluoroscopically.

24. The lead of claim 18 in which:

the outer tube has a lumen defined by an inner cylindrical surface, the inner tube has an outer cylindrical surface, and a diameter of the inner cylindrical surface of the outer tube is substantially the same as a diameter of the outer cylindrical surface of the inner tube.

25. The lead of claim 24 in which:

the inner cylindrical surface of the outer tube directly abuts the outer cylindrical surface of the inner tube.

* * * * *